United States Patent [19]

L'Esperance

[11] 4,435,856
[45] Mar. 13, 1984

[54] BIFOCAL INTRAOCULAR LENS STRUCTURE AND SPECTACLE ACTUATION FRAME

[76] Inventor: Francis A. L'Esperance, 255 Oakwood Rd., Englewood, N.J. 07631

[21] Appl. No.: 368,409

[22] Filed: Apr. 14, 1982

[51] Int. Cl.³ .......................... A61F 1/16; A61F 1/24
[52] U.S. Cl. ............................................ 3/13; 351/57
[58] Field of Search ................... 3/13, 1; 351/54, 57, 351/59, 216, 233

[56] References Cited

U.S. PATENT DOCUMENTS

| | | | |
|---|---|---|---|
| 3,752,567 | 8/1973 | Broadhurst | 351/57 X |
| 4,010,496 | 3/1977 | Neefe | 3/13 |
| 4,056,855 | 11/1977 | Kelman | 3/13 |
| 4,073,014 | 2/1978 | Poler | 3/13 |
| 4,074,368 | 2/1978 | Levy, Jr. et al. | 3/13 |
| 4,187,006 | 2/1980 | Neidell | 351/57 X |
| 4,257,130 | 3/1981 | Bayers | 3/13 |
| 4,298,996 | 11/1981 | Barnet | 3/13 |
| 4,315,337 | 1/1982 | Choyce | 3/13 |
| 4,366,582 | 1/1983 | Faulkner | 3/13 |
| 4,368,958 | 1/1983 | Buget | 351/233 X |

OTHER PUBLICATIONS

Model PC-11 Posterior Chamber, American Medical Optics Advertisement–American Hospital Supply Corp. (4 pages) Aug. 1981.

Primary Examiner—Ronald L. Frinks
Attorney, Agent, or Firm—Hopgood, Calimafde, Kalil, Blaustein & Judlowe

[57] ABSTRACT

The invention contemplates structure for surgical implantation within an eye and providing the user with more than one focal length, for viewing at correspondingly different object ranges. In the embodiments disclosed, one intraocular device is relatively fixed in the eye to provide a conventionally available viewing range, for example, distance viewing, and another lens element is movably mounted with respect to the fixed distance-viewing lens in such manner as to provide its selective use in combination with the fixed lens, for close-object viewing.

24 Claims, 13 Drawing Figures

FIG. 1.
FIG. 2.
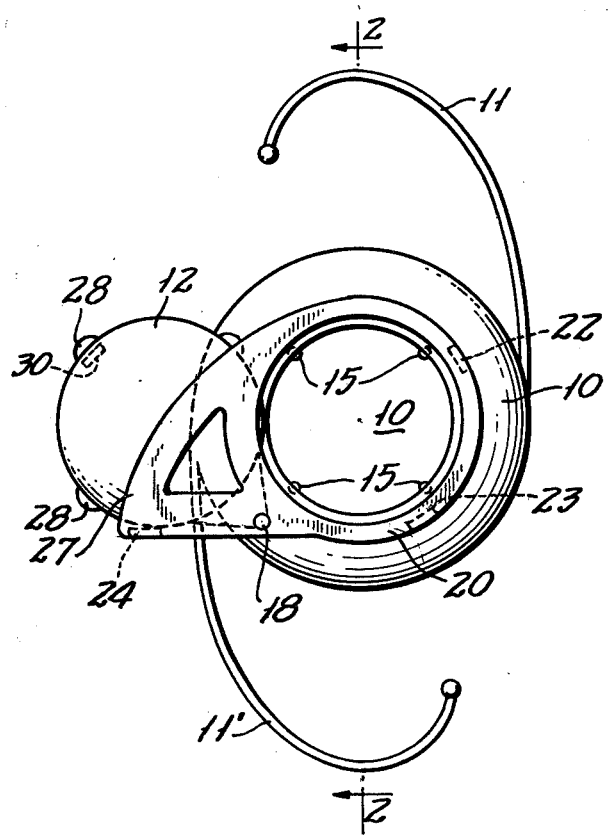
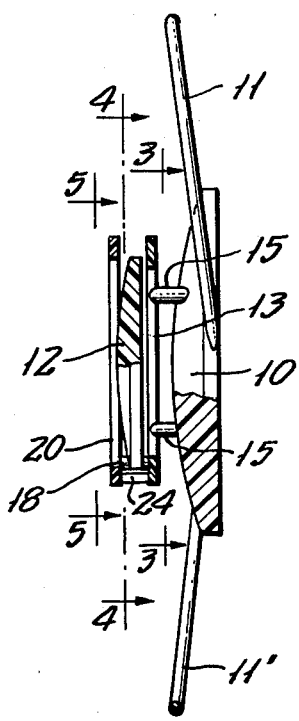
FIG. 3.
FIG. 4.
FIG. 5.
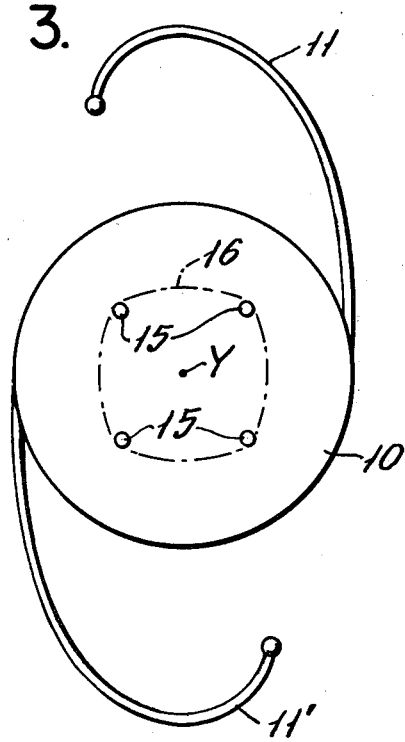
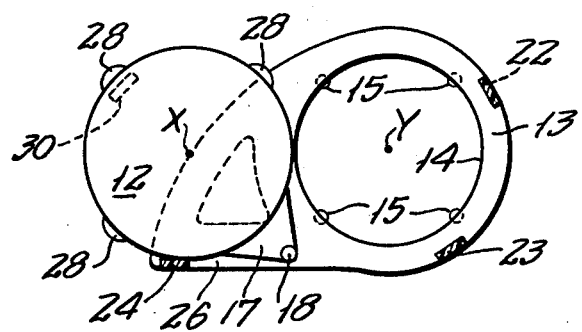
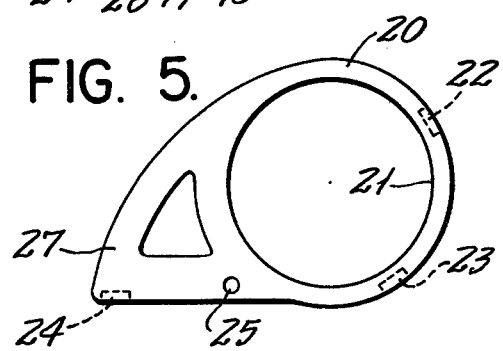

BIFOCAL INTRAOCULAR LENS STRUCTURE AND SPECTACLE ACTUATION FRAME

BACKGROUND OF THE INVENTION

The invention relates to intraocular lens structures, that is, to structures designed and adapted for surgical implantation in an eye, in place of a cataracted natural lens.

Surgical implantation of an artificial lens, in place of a cataracted natural lens, is rapidly becoming an accepted procedure, offering the user the advantage of wide-angle vision and avoidance of the cumbersome strong-lens spectacles that have traditionally been the burden for those who have had a cataract removed. The surgeon has a great variety of lens-implant styles from which to chose, but to my knowledge all such lens-implants to date contemplate but a single focal length of the implant. It is therefore necessary for the user to provide himself with such spectacles as may enable him to correct his vision for any range outside the capability of his fixed-focus implant.

BRIEF STATEMENT OF THE INVENTION

It is an object of the invention to provide improved intraocular lens structure enabling multiple-focus operation within the eye.

A specific object is to provide structure enabling implantation of at least two lenses within a given eye, with selective availability of one to the exclusion of the other of said lenses, to achieve different focal circumstances appropriate to different ranges of desired-object viewing.

Another specific object is to provide structure enabling implantation of an intraocular optical element which is selectively movable into and out of the viewing or pupillary axis of the eye.

A further specific object is to provide externally operable actuator means for selectively positioning an installed intraocular lens into and out of the optical axis of the eye.

A general object is to achieve the above object with relatively simple and low-mass structure which can be surgically manipulated and correctly installed, using present techniques.

The invention achieves the foregoing objects and certain further features by providing haptic-supported frame structure for stabilized mounting in one of the chambers of an eye, and an auxiliary lens or other optical element has movably guided coaction with the frame structure, whereby in one selectively available position the auxiliary element is substantially aligned with the viewing axis of the eye, and in another selectively available position the auxiliary element is substantially out of the bundle of rays used for normal viewing. In the forms to be described, the movable auxiliary element is pivotally suspended and is magnetically actuable from one to the other of its two possible positions. And the forms to be described illustrate various combinations with posterior-chamber mounting, anterior-chamber mounting and trans-iris mounting of the movable element.

DETAILED DESCRIPTION

The invention will be illustratively described in detail, in conjunction with the accompanying drawings, in which:

FIG. 1 is a front-elevation view of intraocular lens structure of the invention;

FIG. 2 is a side-elevation view of the structure of FIG. 1, certain parts being partly broken-away and in vertical section, generally along the line 2—2 of FIG. 1;

Figure 6:
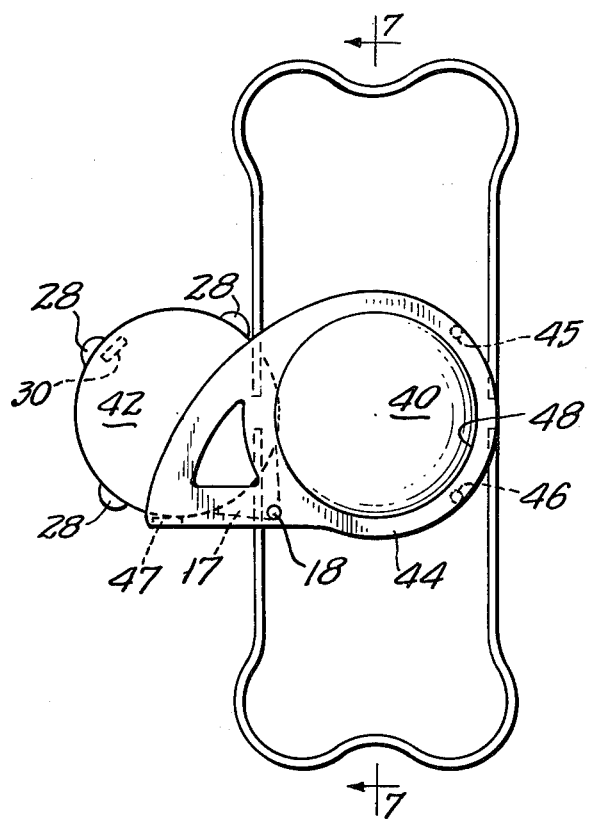
Figure 7:
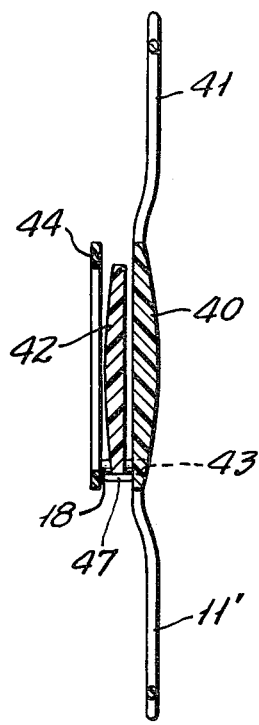
Figure 8:
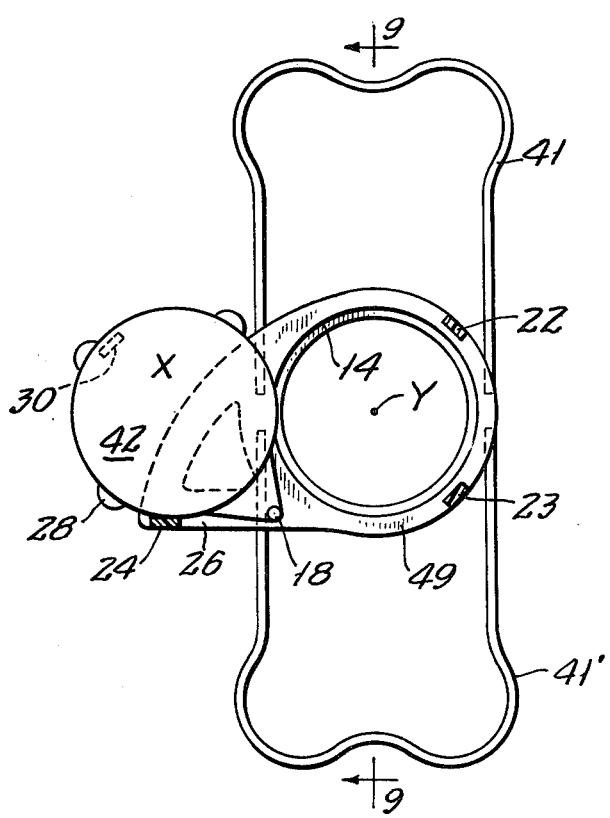
Figure 9:
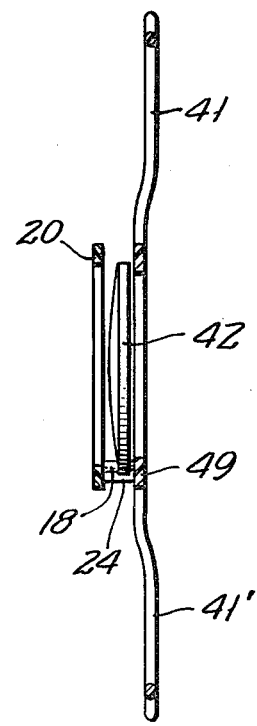
Figure 10:
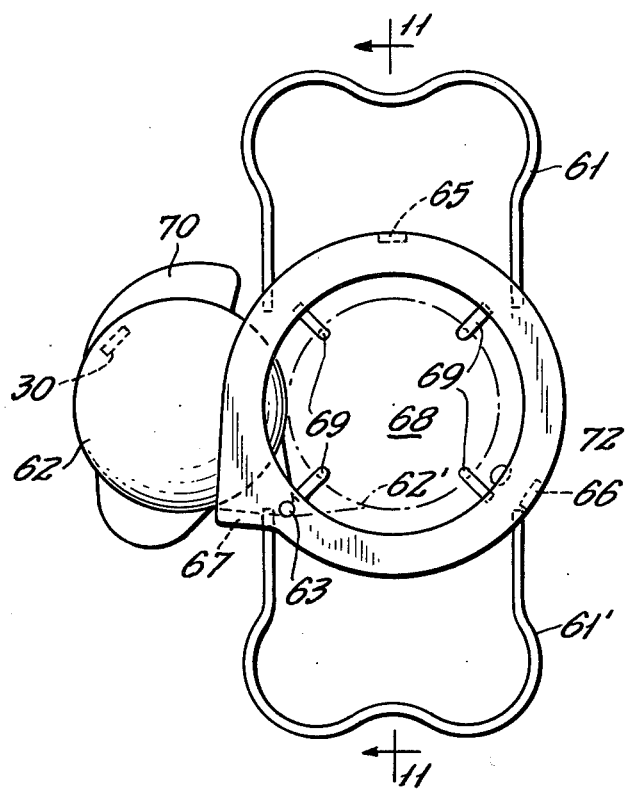
Figure 11:
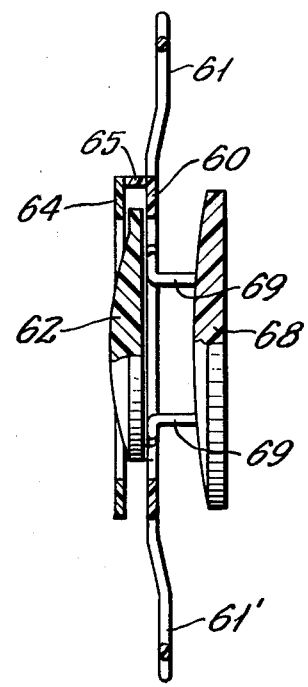
Figure 12:
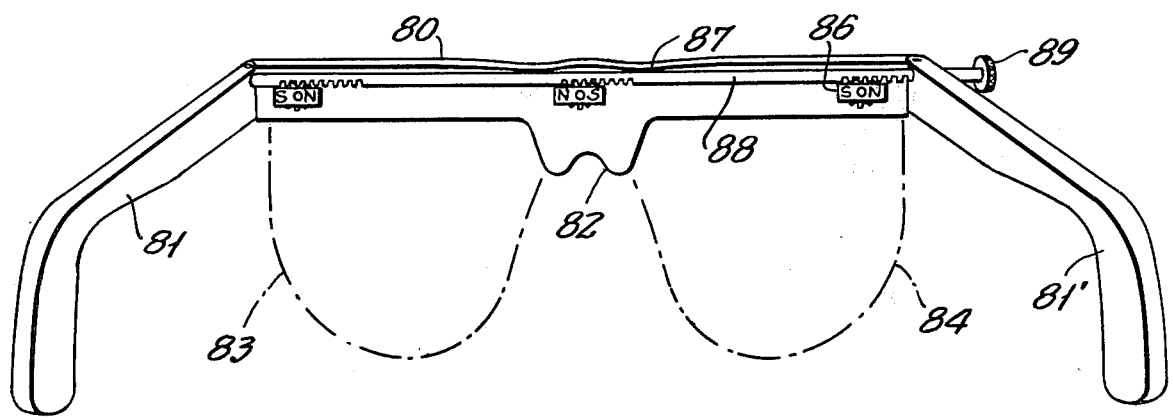
Figure 13:
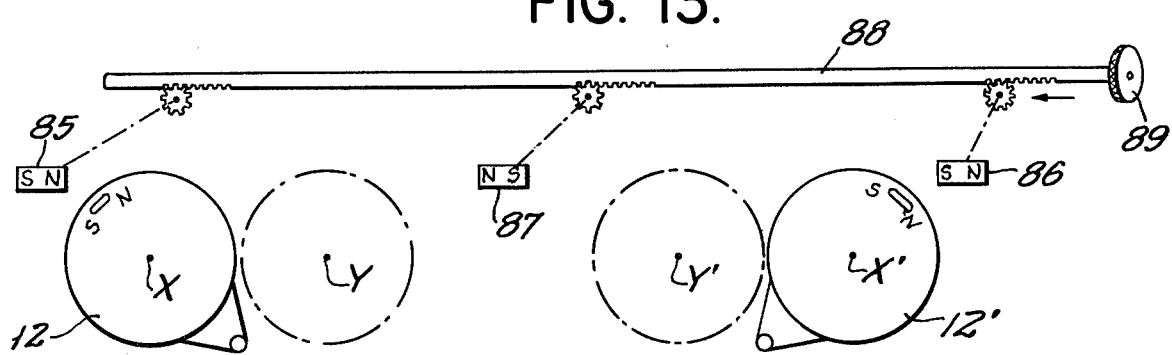

FIGS. 3, 4 and 5 are views taken at successive optical-axis locations in the structure of FIGS. 1 and 2, namely, as indicated at 3—3, 4—4 and 5—5, respectively, in FIG. 2;

FIGS. 6 and 7 are views corresponding to FIGS. 1 and 2 to illustrate another embodiment, the section plane of FIG. 7 being generally at the line 7—7 of FIG. 6;

FIGS. 8 and 9 are views also corresponding to FIGS. 1 and 2, but illustrating a third embodiment, the section plane of FIG. 9 being generally at the line 9—9 of FIG. 8;

FIGS. 10 and 11 are further views corresponding to FIGS. 1 and 2, to illustrate a fourth embodiment, the section plane of FIG. 11 being generally at the line 11—11 of FIG. 10; and FIGS. 12 and 13 are simplified views in perspective to illustrate a non-invasive actuating means for intraocular ocular implants as described for the various embodiments.

Referring initially to FIGS. 1 to 5, the invention is shown in application to a conventional intraocular lens 10 having compliant haptic formations 11-11' adapted particularly for stabilizing contact with the inner wall of the posterior chamber of an eye. The lens 10 may be molded, turned and polished plastic, inert to body fluids, methyl methacrylate being acceptably usable, and the haptic elements may suitably be of polypropylene. Surgical implantation procedure for posterior lens 10 and its haptics may be conventional, via a dilated iris, as will be understood.

In accordance with a feature of the invention, a second optical element, such as another lens 12, is movably supported with respect to the relatively fixed structure of posterior lens 10 and its haptics. More specifically, a frame member 13, which provides pivotal reference for movable lens 12, has a central opening 14 deriving axially forward cantilevered support from the posterior lens 10 via plural trans-iris posts 15, equally spaced about the optical axis Y of lens 10. The forward offset provided by posts 15 will be understood to be sufficient to position frame member 13 within the anterior chamber and with sufficient relief from the iris to allow normal mobility of the iris, i.e., normal dilation with respect to its constricted condition, suggested by phantom outline 16 in FIG. 3.

The movable lens element 12 may be of material and finish as described for lens 10, and it is shown with an integrally formed pivot arm 17 and with a pivot pin 18 engaged in a suitable bearing aperture in frame member 13. A second frame member 20 with a central aperture 21 is connected to frame member 13 via spaced lugs 22-23-24, and in such forwardly offset relation to member 13 as to establish positively guided retention of movable lens 12 by and between frame members 13-20, the opposite ends of pivot pin 18 being located in bearing apertures, as at 25 in frame member 20. It is convenient to provide a laterally extending formation 26 in frame member 13, and 27 in frame member 20, so that lugs 23—24 may connect members 13—20 on opposite sides of the pivot axis and so that lug 24 may serve as a stop, to locate the off-axis position of movable lens 12, as best seen in FIG. 4.

In its off-axis position, the optical axis X of movable lens 12 is preferably at the horizontal elevation of the optical axis Y of lens 10, and preferably also, the axis of pivot 18 is below and on the perpendicular bisector of the geometrical line between X and Y, as seen in FIG. 4. Further, the offset of pivot 18 below the line between X and Y may suitably be such that lens element 12 moves about 90 degrees between its off-axis position (FIG. 4) and its on-axis position of axial alignment with the optical axis Y of the fixed lens element 10. And it will be understood that lugs 22–23 cooperate with movable lens element 12 in its on-axis position, serving as limiting stops. By locating the pivot axis as indicated, and by installing the implant with X and Y on a horizontally oriented alignment, the stop 24 arrests normal gravitational descent of lens 12 to serve as a means of retaining the off-axis position (FIG. 4), while stop 23 arrests normal gravitational descent of lens 12 (on the other side of pivot 18) to serve as a means of retaining the on-axis position of axial alignment of the two lenses 10–12.

Description of the embodiment of FIGS. 1 to 5 is completed by identifying ear projections 28 at spaced locations around movable lens 12, to assure total axial capture of lens 12 by and between rims 14–21 of frame members 13–20 when in the on-axis position. Also, for remote-actuation purposes, a paramagnetic insert 30 is embedded in the material of lens element 12 at greatest radial offset from pivot 18. It will be understood that a permanent magnet (not shown) but embodied for example in a finger ring of the wearer of the structure of FIGS. 1 to 5 may serve to non-invasively actuate the movable lens element 12; he need only draw his magnetic ring across his eyebrow in a desired direction, in order to dislodge movable lens element 12 from one of its two positions and to move it to the other of its two positions.

The embodiment of FIGS. 6 and 7 illustrates application of the invention to an anterior-chamber mounting. In particular, an anterior-chamber "fixed", lens element 40 carries opposed haptic elements 41–11', with suitably vaulted offset ends for minimal iris contact and allowing total freedom for normal mobility of the iris. Lens element 40 is plano-convex and is preferably oriented with its plane surface facing forward, in close adjacency with the plane surface of a movable lens element 42 having arm and pivot formations 17–18 as described for lens element 12 (FIGS. 1 to 5). A bearing aperture 43 in lens 40 mounts one end of pivot 18, and a bearing aperture in a frame member 44 mounts the other end of pivot 18. Spacer posts or lugs 45–46–47 retain the central opening 48 of frame member 44 in register with the optical axis of lens 49 and serve as limit stops for the respective off-axis and on-axis positions of movable lens element 42, analogous to similar functions described for the embodiment of FIGS. 1 to 5. Ears 28 on lens element 42 retain the axially-captured status when in the on-axis position, and magnetic element 30 in movable lens 42 enables selective surgically non-invasive actuation from one to the other of the two limiting positions of lens 42.

The embodiment of FIGS. 8 and 9 is very much like that of FIGS. 6 and 7, except that in place of the fixed lens 40 is a fixed frame member 49 which is equipped by haptic means 41–41' and which may otherwise be generally as described for frame member 13 of FIG. 4, i.e., with a central circular opening 14, with a lateral arm projection 26, and with spaced connecting lugs 22-2-3-24 for positioning a second frame member 20 of the nature shown in FIG. 5; for clarity, frame member 20 is shown in FIG. 9 but has been omitted from FIG. 8. The movable lens element 42 of FIGS. 8 and 9 is guided by and between frame members 20–49 and is non-invasively actuated via an imbedded magnetic element 30. It will be appreciated that the embodiment of FIGS. 8 and 9 may serve the patient who already has a posterior-chamber implanted lens (as, for example, shown in FIG. 3 but without posts 15) and for whom it is desired to provide selectably extendable focal range, by reason of anterior-chamber implantation of the device of FIGS. 8 and 9, with opening 14 centered on the pupillary axis Y.

The embodiment of FIGS. 10 and 11 exemplifies the invention in application to anterior-chamber mounting, of a frame member 60 via vaulted haptics 61–61' with reference to the stationary or scleral-ridge region of the anterior-chamber side of the iris. A movable lens element 62 includes a pivot pin 63 which derives bearing support from aligned apertures in frame member 60 and in an outer frame member 64, frame members 60–64 being held in axially spaced register by spacer posts or lugs 65–66–67. A "fixed" posterior lens element 68 derives axially aligned cantilevered support from frame member 60, via angularly spaced trans-iris positioning struts 69. Each of the struts will be understood to be L-shaped, with a radially inward leg portion anchored to frame member 60, and with an axially inward trans-iris portion anchored to lens element 68. Outward ear projections 70–71 on movable lens element 62 will be understood to axially restrain the on-axis position of element 62. The on-axis angular position is retained by a stop lug or pin 72 on one of the frame members 60–64, and the off-axis position is retained by lug 67, as will be understood.

While it has been indicated that actuating structure for the described movable-lens configurations may be as simple as a polarized magnet embodied in a finger ring, it may to some users be more convenient to embody magnetic control in a spectacle frame, whether or not there are optical lens elements fitted to the spectacle frame. Such structure and its operation are shown in the simplified views of FIGS. 12 and 13. In FIG. 12, a spectacle frame is seen to comprise a transverse member 80, with hinged ear pieces 81–81' at its ends; a suitably shaped central bridge formation 82 is comfortably adapted to the nose, and optional lens elements are suggested by phantom outlines 83–84. In accordance with a feature of the invention, polarized magnets 85–86 are reversibly mounted to the spectacle frame, being shown pivotally mounted near the ends of member 80, and preferably a third such magnet 87 is similarly mounted in the bridge region of member 80. These magnets may be of any suitable shape, for example pinion-shaped and polarized along a diameter, but for schematic purposes these magnets are shown as bars, with pinion teeth, and polarized as suggested by N-S symbolism. A shiftable member 88 with rack teeth engaged to magnet-pinion teeth has an exposed actuable element 89 for selecting either the polarity relation shown or a 180°-reversed polarity configuration, as will be understood.

The described spectacle frame with reversible magnets is shown in FIG. 13 to effect desired actuation of movable-lens elements 12 (in one eye's intraocular implantation) and 12' (in the other eye's intraocular implantation). In the left-eye implantation, the on-axis position of movable-lens axis X registration with fixed-lens axis Y is inward, toward the nose, and the off-axis position is outward, toward the adjacent ear piece 81; and in the right-eye implantation, the on-axis position of movable-lens axis X' registration with fixed-lens axis Y' is inward, toward the nose, the off-axis position being outward toward ear piece 81' and, therefore, in the displacement direction away from off-axis displacement of lens axis X for the left eye. Magnet inserts 30 in the respective movable-lens elements 12-12' are polarized alike, as shown by N-S symbolism, the axis of polarization being transverse of the central line of symmetry of each element 12-12', i.e., through its pivot center 18 and the center of its magnet insert 30.

For the described configuration of insert 30 polarization and of off-axis to on-axis displacements for movable lens elements 12-12', the polarized orientation of outer magnets 85-86 should always be opposed to that of the central magnet 87. That being the case, for the relation shown in FIG. 13, the off-axis or outward-left position of lens element 12 is magnetically retained by proximity of the North-polarized end of magnet 85 and the South-polarized end of the involved insert 30. At the same time, the off-axis or outward-right position of lens element 12' is magnetically retained by proximity of the South-polarized end of magnet 86 and the North-polarized end of the involved insert 30. Also at the same time, the orientation of central magnet 87 is such as to present like poles to the nearest poles of elements 30, thus developing repel action for further assured retention of the off-axis positions of both movable lens elements 12-12'.

When it is desired to bring both movable lens elements into their on-axis positions of registration with the respective pupillary axes Y-Y', the shift device 89 is manually displaced, causing magnets 85-86-87 to 180°-reverse their polarized orientation. In this circumstance, like adjacent poles (the South poles of magnet 85 and the nearby insert 30) repel to develop clockwise torque about the pivot axis of movable element 12, resulting in its left-to-right displacement into the on-axis position of registration with axis Y; and upon reaching this on-axis position, the attraction of opposite poles at 30 and 87 serves to retain the on-axis position of element 12. In similar fashion and concurrently, like adjacent poles (the North poles of magnet 86 and of nearby insert 30) repel to develop counterclockwise torque about the pivot axis of movable element 12', resulting in its right-to-left displacement into the on-axis position of registration with axis Y'.

Subsequent return of actuator 89 to the position shown returns all rotatable magnets to their orientations shown, and resulting torques on the movable lens elements 12-12' effect concurrent return displacements to and magnetic retention of the respective off-axis positions.

The described invention will be seen to achieve all stated objects with basically simple and lightweight structure. And the principles of the invention are seen to be applicable to varied anterior, posterior, and trans-iris support, to suit the choice of the individual surgeon. The involved implantation technique need be no more difficult or complex than for conventional single-lens implantations. It will, of course, be understood that in the drawings it was necessary to show sizes, thicknesses and clearances with some exaggeration, in order to permit identification of parts; for example, the displacement sweep of lens element 12 from one to the other of its positions is under the continuous guidance not only of the described pivot (18) action but also of surfaces of frame members 13-20 (FIGS. 1 to 5), or of lens 40 and frame member 44 (FIGS. 6, 7), etc.

While the invention has been described in detail for preferred embodiments, it will be understood that modifications may be made without departure from the scope of the invention. For example, guided shifting of movable lens elements may be longitudinal and thus other than via a pivot suspension, and reversible magnet elements in the spectacles may be carried by the ear pieces and be individually shiftable to effect selective reversal of their horizontally polarized directions.

What is claimed is:

1. Intraocular lens structure, comprising a first lens element including haptic means for stabilized mounting of the lens in one of the chambers of an eye and substantially on the pupillary axis of the eye, a second lens element, means coacting between off-axis locations of said lens elements for pivotally suspending said second lens element at axial offset with respect to said first lens element, means coacting between said lens elements for selective retention of (1) a pivoted position of said second lens element wherein the optical axes of said lens elements are in substantial registration and (2) a pivoted position of said second lens element wherein said second lens element is substantially offset from the axis of said first lens element, and means associated with said second lens element and adapted to facilitate selective pivoted displacement from one to the other of said positions.

2. The intraocular lens structure of claim 1, and including guide elements carried by said first lens element and engageable with axially opposite ends of said second lens element for stabilizing said second lens element against axial dislocation throughout the range of pivotable displacement.

3. Intraocular lens structure, comprising a haptic frame member having a central opening, haptic leg structure associated with said frame member at angularly spaced locations and extending generally radially with respect to said frame member for eye-chamber wall engagement to position the opening substantially on the pupillary axis of an eye and adjacent the iris of the eye, a lens element including a radially outwardly extending arm, means pivotally suspending said lens element via said arm and via a pivot axis in said frame member, the pivot axis being parallel to the eye axis of the opening, means coacting between said frame member and said lens element for selective retention of (1) a pivoted position of said arm wherein the lens-element axis coincides with the eye axis of the opening and (2) a pivoted position of said arm wherein said lens element is substantially offset from registration with said frame-member opening, and means associated with said lens element and adapted to facilitate selective pivoted displacement of said lens element from one to the other of said positions.

4. The intraocular lens structure of claim 3, in which a second lens element is supported by said haptic frame member to retain the optical axis of the second lens element substantially on the pupillary axis of the eye and at axial offset from said pivotally suspended lens element.

5. The intraocular lens structure of claim 3, in which said haptic frame member includes guide elements engageable with axially opposite ends of said lens element for stabilizing said lens element against axial dislocation throughout the range of pivotable displacement.

6. Intraocular lens structure, comprising a posterior-chamber lens including haptic means for stabilized mounting of the lens in the posterior chamber of an eye and on the pupillary axis and near the iris of the eye, a frame member having a central opening and trans-iris supporting means connecting said frame member to said lens at such forward offset from said lens as to retain said frame in the anterior chamber of the eye and with the frame opening on the pupillary axis, a lens element including a radially outwardly extending arm, means pivotally suspending said lens element via said arm and via a pivot axis in said frame member, the pivot axis being parallel to the axis of said posterior-chamber lens, means coacting between said frame member and said lens element for selective retention of (1) a pivoted position of said arm wherein the lens-element axis coincides with the axis of the posterior-chamber lens and (2) a pivoted position of said arm wherein said lens element is substantially offset from registration with said frame-member opening, and means associated with said lens element and adapted to facilitate selective pivoted displacement from one to the other of said positions.

7. The intraocular lens structure of claim 1 or claim 3 or claim 6, in which said lens element is an optical filter.

8. The intraocular lens structure of claim 1 or claim 3 or claim 6, in which said last-defined means is a permanently magnetized element fixedly carried by the pivotally suspended lens element at a location radially offset from the pivot axis.

9. The intraocular lens structure of claim 1 or claim 3 or claim 6, in which said pivoted element and an unpivoted part of said structure coact to at least yieldably retain a selected one of said pivoted positions.

10. The intraocular lens structure of claim 1 or claim 3 or claim 6, in which an unpivoted part of said structure in the region of the axis of pivotal suspension is exposed for viewability prior to eye implantation, whereby the lens structure may be implanted in an eye with the pivotal axis at a location beneath the pupillary axis and offset horizontally therefrom to substantially one half the extent of pivoted-element displacement between said positions; further whereby, in a normally erect posture of the wearer of the implant, each of said positions, once attained, will be at least yieldably retained by gravitational action.

11. Intraocular lens structure, comprising a first lens element including haptic means for stabilized lens mounting in substantial optical alignment with the pupillary axis of an eye, a second lens element retained at axial offset from said first lens element and movably mounted with respect thereto, means coacting between said lens elements and limiting such movement between a first position of substantial optical-axis alignment of said lens elements and a second position of substantial removal of said second lens element from the path of acceptance rays of said first lens element, and means associated with said second lens element and adapted to facilitate selective displacement from one to the other of said positions.

12. In combination, the intraocular lens structure of claim 11, wherein said last-defined element is a permanently magnetized slave element fixedly carried by said second lens element, and an externally manipulable, permanently magnetized master element in displacement-force-reacting relation with said second lens element via said slave element when non-invasively proximate to said slave element.

13. The combination of claim 12, in which means including a spectacle frame is adapted for wear by the recipient of an installation of said lens structure, said master element being reversibly mounted in a part of said spectacle frame.

14. A spectacle frame including transversely extending means adapted to support spectacle-lens elements at prescribed interpupillary spacing, and a horizontally polarized magnet element selectively reversibly mounted to said frame between lens-element supporting regions, the reversibility being as to the transverse direction of horizontal polarization, whereby selective reversal of oppositely polarized magnetic fields may be directed in the regions of the eyes of the wearer of the spectacles, for selective non-invasive action upon magnetically responsive means within the respective eyes.

15. A spectacle frame including transversely extending means adapted to support spectacle-lens elements at prescribed interpupillary spacing, and a horizontally polarized magnet element selectively reversibly mounted to same frame at a location transversely outside the pupillary alignment for one of the lens-element supporting regions, the reversibility as to the transverse direction of horizontal polarization, whereby selective reversal of opposite polarized magnetic fields may be directed in the region of the involved eye of the wearer of the spectacles, for selectively non-invasive action upon magnetically responsive means within the involved eye.

16. A spectacle frame including transversely extending means adapted to support spectacle-lens elements at prescribed interpupillary spacing, a first horizontally polarized magnet element selectively reversibly mounted to said frame between lens-element supporting regions, and a second horizontally polarized magnet element selectively reversibly mounted to said frame at a location transversely outside the pupillary alignment for one of the lens-element supporting regions, whereby selective reversal of the fields of said magnets may non-invasively determine selected response of magnetically responsive means within the eye between said magnets.

17. The spectacle frame of claim 16, in which linkage means coordinates polarity reversal of said magnets such that their adjacent poles are always of opposed polarity.

18. The spectacle frame of claim 16, and including a third horizontally polarized magnet element selectively reversibly mounted to said frame at a location transversely outside the pupillary alignment for the other of the lens-element supporting regions.

19. The spectacle frame of claim 18, in which linkage means coordinates polarity reversal of said magnets such that adjacent poles of adjacent magnets are always of opposed polarity.

20. Intraocular lens structure according to claim 3, in which said frame member is one of two frame members having aligned central openings and means retaining said frame members in such axially spaced relation as to accommodate retention of said lens element therebetween, the pivotal suspension being from both frame members.

21. Intraocular lens structure according to claim 20, in which stop means carried by one of said frame members extends into the space between said frame members and into the path of pivoted movement of said lens element at locations determining limits of movement between said pivoted positions.

22. Intraocular lens structure, comprising an anterior-chamber lens including haptic means for stabilized mounting of the lens in the anterior chamber of an eye and on the pupillary axis and near the iris of the eye, a frame member having a central opening on the pupillary axis and means supporting said frame member at forward offset from said lens, a second lens and means pivotally suspending said second lens from both said anterior-chamber lens and said frame member, the pivotal axis being off the optical axis of each of said lenses such that in one pivoted relation the optical axes are in registering alignment and in another pivoted relation said second lens is substantially offset from registration with said frame-member opening, and means associated with said second lens and adapted to facilitate selective pivoted displacement from one to the other of said positions.

23. The intraocular lens structure of claim 22, in which first and second lenses are each plano-convex, mounted with their flat sides in opposed adjacency.

24. Intraocular lens structure, comprising first and second frame members each having a circular viewing opening and means retaining said frame members in axially spaced relation and with their viewing openings on the same axis, anterior-chamber haptic means on one of said frame members for stabilized mounting of said frame members in the anterior chamber of an eye and on the pupillary axis and near the iris of the eye, a posterior-chamber lens and trans-iris supporting means connecting said lens to the nearer one of said frame members and at such rearward offset from said nearer frame member as to retain said lens in the posterior chamber of the eye and with said lens and frame openings on the pupillary axis, an auxiliary lens pivotally suspended from and between said frame members, the axis of said pivotal suspension being off the optical axis of each of said posterior and auxiliary lenses such that in one pivoted relation the optical axes are in registering alignment and in another pivoted relation said auxiliary lens is substantially offset from registration with said frame-member openings, and means associated with said auxiliary lens and adapted to facilitate selective pivoted displacement from one to the other of said positions.

* * * * *